United States Patent
Brindle et al.

[11] Patent Number: 6,143,416
[45] Date of Patent: Nov. 7, 2000

[54] POLYURETHANE THIN-WALLED ARTICLES WITH A ROUGH SURFACE, AND METHOD OF PRODUCING THE SAME

[75] Inventors: Philip Wayne Brindle, Ely; Thomas Haydn Williams, Cambridge, both of United Kingdom

[73] Assignee: LRC Products Limited, United Kingdom

[21] Appl. No.: 09/202,362

[22] PCT Filed: Jun. 12, 1997

[86] PCT No.: PCT/GB97/01595

§ 371 Date: Jan. 25, 1999

§ 102(e) Date: Jan. 25, 1999

[87] PCT Pub. No.: WO97/47451

PCT Pub. Date: Dec. 18, 1997

[30] Foreign Application Priority Data

Jun. 13, 1996 [GB] United Kingdom .................. 9612324

[51] Int. Cl.⁷ .................................................. A41D 19/015
[52] U.S. Cl. ..................................... 428/423.1; 428/423.3; 427/385.5; 2/161.8; 2/167
[58] Field of Search ................. 2/161.8, 167; 427/385.5; 428/423.1, 423.3

[56] References Cited

U.S. PATENT DOCUMENTS

| | | | |
|---|---|---|---|
| 723,301 | 3/1903 | Pfeiffer | 2/160 |
| 919,406 | 4/1909 | Warren | 2/160 |
| 2,120,406 | 6/1938 | Hansen | 2/160 |
| 2,173,734 | 9/1939 | Sidnell | 2/168 |
| 2,393,298 | 1/1946 | De Laney et al. | 2/160 |
| 2,581,248 | 1/1952 | Ganz | 156/214 |
| 2,581,249 | 1/1952 | Ganz | 2/168 |
| 2,631,108 | 3/1953 | Timmons | 427/133 |
| 3,255,492 | 6/1966 | Velonis et al. | 606/23 |
| 3,883,899 | 5/1975 | Ganz | 2/167 |
| 4,329,312 | 5/1982 | Ganz | 264/306 |
| 4,660,228 | 4/1987 | Ogawa et al. | 2/167 |
| 5,088,125 | 2/1992 | Ansell et al. | 2/167 |
| 5,391,343 | 2/1995 | Dreibelbis et al. | 264/216 |
| 5,650,225 | 7/1997 | Dutta et al. | 2/168 |
| 5,881,386 | 3/1999 | Horwege et al. | 2/167 |

FOREIGN PATENT DOCUMENTS

| | | |
|---|---|---|
| 0 089 780 | 9/1983 | European Pat. Off. . |
| 0 326 032 | 8/1989 | European Pat. Off. . |
| 0 482 618 | 4/1992 | European Pat. Off. . |
| 9899 | 2/1901 | United Kingdom . |
| 782 520 | 9/1955 | United Kingdom . |
| 1 073 601 | 6/1967 | United Kingdom . |
| 1 310 711 | 3/1970 | United Kingdom . |
| 1 235 282 | 6/1971 | United Kingdom . |
| 1 326 102 | 8/1973 | United Kingdom . |
| 1 549 351 | 5/1975 | United Kingdom . |
| 2 181 691 | 4/1987 | United Kingdom . |
| 94/20574 | 9/1994 | WIPO . |
| 96 08353 | 3/1996 | WIPO . |

OTHER PUBLICATIONS

Patent Abstracts of Japan, vol. 008, No. 249(M–338), Nov. 15, 1984, abstracting JP 59 124832 A, dated Jul. 29, 1984, St Kagaku Kogyo KK.

*Primary Examiner*—Rachel Gorr
*Attorney, Agent, or Firm*—Rankin, Hill, Porter & Clark LLP

[57] ABSTRACT

A method of forming a thin-walled article, namely a surgeon's glove, having an outer grip coating of a first elastomer on a high modulus polyurethane substrate, wherein the outer coating has a rough surface to provide surface grip and the polyurethane substrate provides the majority of the glove's thickness, the method including coating a roughened former with a first elastomer that substantially does not retain bubbles that may be formed; coating a high modulus polyurethane to the coated former to form the main body of the article; drying and/or curing the composite article; and stripping the composite article from the former, whereby the surface of the first elastomer has a rough surface to provide surface grip. A surgeon's glove including an outer grip coating of a first elastomer on a high modulus polyurethane substrate, wherein the coating has a rough surface to provide surface grip and the polyurethane layer provides the majority of the glove's thickness.

20 Claims, 1 Drawing Sheet

POLYURETHANE THIN-WALLED ARTICLES WITH A ROUGH SURFACE, AND METHOD OF PRODUCING THE SAME

This invention relates to polyurethane articles, particularly to thin-walled articles made by dipping, and especially (but not exclusively) to gloves of the sort used by surgeons.

For many years past, it has been known to make surgeon's gloves from natural rubber latex. The gloves so made have a number of very satisfactory properties and are very widely used. However, natural rubber contains small amounts of protein and accelerators and it is believed that this may possibly give rise to allergies in users of the gloves. For this and other reasons, attention has passed to the possibility of using elastomers other than natural rubber.

One alternative material is polyurethane. Polyurethanes are available which have a higher modulus than natural rubber and these materials can be used to make gloves which are thinner than natural rubber gloves and have a higher tensile strength. However, these stiffer polyurethanes are too hard to give a good surface grip. They tend to have a shiny surface which, particularly in moist or wet conditions, is slippery. It is, of course, very important that articles such as surgeons' gloves should have good grip surfaces, especially in moist and wet conditions.

It is known to improve the grip of surgeons' gloves by providing a roughened outer surface to the gloves. This technique is described, for example, in U.S. Pat. No. 3,255,492. Here, a matt surface is provided on the outer surface of a glove by using a dipping former whose surface has been roughened such as by caustic etching, vapour blasting, sand blasting, anodizing or the like. The U.S. specification is principally concerned with polyvinylchloride gloves, but it also refers to the possibility of making certain polyurethane gloves in this way.

We have investigated the use of roughened formers to provide roughened outer surfaces on polyurethane gloves, but we have found that in practice, there is a serious practical problem with this technique as applied to organic solutions of high modulus polyurethanes. In particular, the roughened surface of the former promotes the formation of bubbles in the polyurethane coating on the former. These bubbles tend to remain in the coating and to give rise to various problems, including problems in the integrity of the coating.

We have now found a way of overcoming this, whereby a roughened outer grip surface can be provided on polyurethane dipped articles by using a roughened former.

According to a first aspect of the present invention there is provided a method of forming a thin-walled article, which method comprises coating a roughened former with a first elastomer, which first elastomer substantially does not retain any bubbles that may be formed; coating a high modulus polyurethane to the coated former to form the main body of the article; drying and/or curing the composite article; and stripping the composite article from the former, whereby the surface of the first elastomer has a rough surface to provide surface grip.

In this way, the polyurethane glove (or other article) has a roughened grip surface derived from the effect of the roughened former, without the problem of bubble formation in the polyurethane.

In the preferred embodiment, the first elastomer is coated on the former by dipping the former into the first elastomer. Similarly, the high modulus polyurethane is preferably coated on the former by dipping the former into said polyurethane.

According to a second aspect of the present invention, there is provided a thin-walled article comprising a grip coating of a first elastomer on a high modulus polyurethane substrate, wherein the coating has a rough surface to provide surface grip.

The polyurethane will normally be a thermoplastic polyurethane (although curable polyurethanes can be used) and will normally have a modulus (i.e. a modulus at 100%) extension of at least about 2 MPa, but usually no greater than about 5 MPa. There are many commercially available polyurethanes which may be used, including for example polyether polyurethanes (e.g. Avalon 80 AT), polyester polyurethanes (e.g. Avalon 70 AE, Estane 5710, Ellastolan 80A); polycaprolactone polyurethanes (Avalon 75AC) (Avalon products are available from ICI, Estane products from BFG, and Ellastolan products from BASF).

The high modulus polyurethanes used in the invention are normally in organic solvent solutions, but some water-based polyurethanes can be used.

The articles of the invention may be made for example by dipping a roughened former into a solution or dispersion of the grip coating elastomer and then into a solution or dispersion of the polyurethane material. The gloves (or other articles) are turned inside out upon removal from the former. Since manufacture of laminated thin-walled articles in this general way is well known in the art, further detailed description will not be given.

The elastomer grip coating which is applied on to the roughened surface of the former, substantially does not retain any of the bubbles which may be formed. Preferably, an aqueous dispersion is used which will normally not give rise to any bubble formation. However, organic solvent solutions or dispersions can be used but the solution or dispersion will preferably have a relatively low viscosity so that any bubbles which are formed will escape therefrom during and after dipping, and when drying. For this purpose, we prefer the viscosity to be no more than about 800 cps (8 $Nm^{-2}s$) and preferably below 600 cps (6 Nm–2s), measured on a Brookfield viscometer at a speed of 12 rpm using an LV2 spindle at 25° C.±2° C.). In this way, any tendency to bubble formation in the grip coating will not give rise to particular problems. The final grip coating will preferably be completely free of bubbles.

The elastomer grip coating serves by its roughened surface to provide grip. However, according to a highly preferred feature of the invention, the elastomer will be chosen to provide other properties not available in the high modulus polyurethane. Thus, we prefer that the elastomer used to provide the surface coating be softer than the substrate polyurethane. For example, we prefer it to have a modulus of less than about 3 MPa and more preferably less than about 2 MPa. Most preferably, it will be predominantly hydrophobic and possess a high coefficient of friction.

Suitable coating polymers include soft polyurethanes, block copolymers such as styrene-isoprene-styrene or styrene-ethylene-butylene-styrene, natural rubber, polyvinylchloride (PVC), synthetic rubbers such as silicone, acrylic, nitrile and polychloroprene. For the best adhesion between the coating and the underlying hard polyurethane, we prefer to use a coating of polyurethane, styrene-ethylene-butylene-styrene or self-crosslinking acrylonitrile latex. Highly preferred coating materials are soft, aliphatic, aqueous polyurethane dispersions, such as Quilastic 148-56 from Merquinsa (Spain).

According to a further preferred feature of the invention, we use a thermoset polymer for the grip coating. This gives the gloves increased solvent resistance which is a significant advantage. An example of a thermoset polymer for this purpose is a self-crosslinking polyurethane latex, e.g. Milloxane 280 (available from Polyurethane specialists).

The grip coating should preferably be a non-newtonian fluid and exhibit a fair degree of pseudoplasticity to reduce the risk of defects occurring during application. The grip coat will preferably have a lower specific heat capacity than the former, so that heat is dissipated more effectively in the micro-environment of the post coating interface. It is also preferred that the grip coat should be at such a solids content as to create a smoothing effect on the former surface so that there are no nucleation points for bubble formation when the high modulus polyurethane is applied thereover. As will be understood, the grip coating must be chemically compatible with the high modulus polyurethane coating and not adversely affected by solvent diffusion.

The polyurethane gloves and other articles of the present invention combine the advantages of hard polyurethanes, namely high strength and low thickness, with the surface grip advantages of a roughened surface elastomer.

Standard production surgeons' glove formers are known in three different surface finishes, these are glazed (essentially smooth), biscuit or bisque finish (non-glazed, quite rough as they appear from the cast) and macro-roughened (particles in the glaze effect a roughening of, most commonly, about 40 micrometers). Whilst the biscuit and micro-roughened formers can be used in accordance with the present invention, we have found that it is preferable to use a former which has been very finely roughened In particular, we prefer to use glazed porcelain formers which have been blasted at 60 to 100 psi ($0.41 \times 10^6$ to $0.69 \times 10^6$ Pa), preferably around 80 psi ($0.55 \times 10^6$ Pa), with an abrasive, such as alumina, of particle size in the range 10 to 50 micrometers mean diameter. One preferred material is Alumina 400 which has 17 micrometers mean diameter particles. This treatment gives the former a very finely roughened angular finish with a matt appearance. Whilst this is our currently preferred method of making the special formers, it may be possible to make them in other ways and the invention is not limited to the particular blasting method described above.

The finely roughened formers which we prefer to use have a surface roughness which can be measured using a "Tally-Surf" probe instrument. The resulting International Parameter of Roughness, otherwise called the Ra value or mean peak to valley height, is generally in the range of about 0.5 to about 1.5 micrometers, preferably about 1.0 micrometer. The distance between profile peaks at the measured mean line (Sm) is generally in the range 30 to 70 micrometers, preferably about 50 micrometers.

The accompanying drawings illustrate, by way of example only, "Tally-Surf" graphs from typical formers, where FIG. 1 is of a macro-roughened straight finger former (Ra=8.0, Sm=428 µm);

Figure 1:
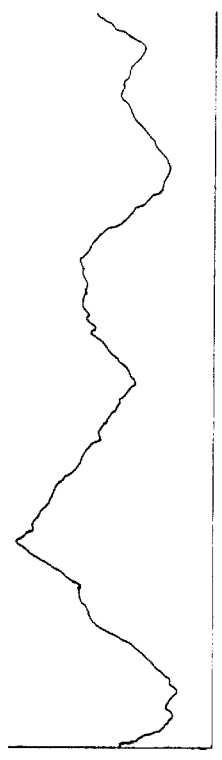
Figure 2:
FIG. 2 is of a bisque curved finger former (Ra=7.0, Sm=428 µm)
Figure 3:
FIG. 3 is of a euroclay smooth porcelain former (Ra=2.0, Sm=60.0 µm)
Figure 4:
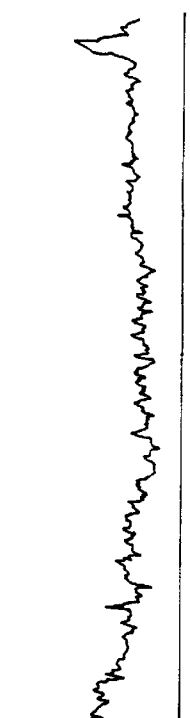
FIG. 4 is of a former treated in accordance with the present invention (Ra=1.0, Sm=49.0 µm).

The essential differences between the results for the four different formers will be self-evident. The finely roughened surface of FIG. 4 is in sharp contrast to the surfaces of the other three Figs. The finely roughened formers described for use in the present invention constitute per se a further aspect of the invention.

The degree of roughening of the formers of the invention can be varied to suit the characteristics of the surface coating being used, to provide the desired grip performance. Routine trial and experiment will enable optimum conditions to be established in any particular case. In general, the use of the finely roughened formers of the invention gives the gloves (or other articles) a matt finish which is aesthetically pleasing. It also greatly reduces the tack of the surface coating.

The formers also provide an important processing advantage in the manufacture of the articles of the invention.

In order that the invention may be more fully understood, the following Example is given by way of illustration only.

EXAMPLE

Gloves were made by dipping two formers first into an elastomer dispersion (to form the outer grip coating) and then into an aromatic thermoplastic solution grade polyurethane to form the main body of the glove. The materials used, and the different formers, are identified below. For comparison, gloves were also made from the polyurethane only (no surface coating).

The gloves so formed were examined for visual appearance and for surface tack. They were then tested for grip under wet and dry conditions. The results were as follows.

1. Glazed Former

| (a) Polyurethane only: | very tacky, almost unstrippable from former, shiny and unpleasant appearance. |
|---|---|
| (b) Polyurethane and grip coating: | tacky, shiny appearance. |

2. Finely Roughened Former (According to Invention)

| (a) | Polyurethane only: | non-tacky, harsh feel, matt finish, some bubbling evident. |
|---|---|---|
| | Mean dynamic friction coefficient measured on Plint Friction Tester TE75: | dry 0.40 wet 0.46 |
| | Mean volume test (ml); contact angle (sessile drop method). | dry 790 wet 450 153° |
| (b) | Polyurethane and grip coating: | non-tacky, felt very "grippy", matt finish, pleasant soft feel. |
| | Mean dynamic friction coefficient measured on Plint Friction Tester: | dry 1.45 wet 1.50 |
| | Mean Volume test (ml): Contact angle (sessile drop method). | dry 910 wet 825 153° |

The mean volume test is a subjective test where panel members grip a 1 liter measuring cylinder with a gloved hand. Water is poured into the cylinder until slippage is observed.

As can be seen from the above results, the combination of grip coating and finely roughened former provide a glove of superior grip and tack properties as compared to gloves made on glazed (smooth) formers and to gloves made only of the hard polyurethane.

Materials (i) Elastomer Dispersion (for Grip Coating)

The elastomer dispersion was prepared by taking the high solids elastomer latex Milloxane 280 (ex PU Specialities, New Jersey, USA) and diluting to 10% with deionised water. The systems rheology was controlled by the addition of 0.2% Xanthan gum thickener.

(ii) Polyurethane Solution

Thermoplastic polyurethane granules, Ellastolan 80A, were dissolved in tetrahydrofuran solvent until a 20% solids dip solution was obtained.

(iii) Glazed Former

Standard glazed surgeons glove formers were used (e.g. as may readily be obtained from Wade Ceramics of Stoke-on-Trent).

(iv) Finely Roughened Former

The finely roughened former was obtained by blasting a standard glazed former with alumina particles of 17 μm mean diameter at a pressure of approximately 80 psi ($0.55 \times 10^6$ Pa).

Method

Gloves are made by the following steps:

1. The former was dipped into a bath of the elastomer dispersion (grip coat), and then withdrawn and the coating dried.
2. The coated former was then dipped into the polyurethane solution and then withdrawn. A bead was formed in the conventional way and the polyurethane coating dried.
3. The former was then dipped in hot water for 10 minutes, after which the glove so formed was stripped from the former and dried.

What is claimed is:

1. A method of forming a thin-walled article, namely a surgeon's glove, comprising an outer grip coating of a first elastomer on a high modulus polyurethane substrate, wherein said outer coating has a rough surface to provide surface grip and said polyurethane substrate provides the majority of the glove's thickness, which method comprises:

coating a roughened former with a first elastomer, which first elastomer substantially does not retain any bubbles that may be formed;

coating a high modulus polyurethane to the coated former to form the main body of the article;

drying and/or curing the composite article; and stripping the composite article from the former, whereby the surface of the first elastomer has a rough surface to provide surface grip.

2. A method according to claim 1, wherein the former is coated with a dispersion or solution of the first elastomer in an aqueous or organic dispersant or solvent.

3. A method according to claim 2, wherein the concentration of the first elastomer in the dispersion or solution is sufficient to create a smoothing effect on the former surface so that there are no nucleation points for bubble formation when the coated former is coated with polyurethane.

4. A method according to claim 1, wherein the first elastomer is soft polyurethane, a block copolymer, natural rubber, polyvinylchloride (PVC), synthetic rubber or a thermoset polymer.

5. A method according to claim 1, wherein the first elastomer is a soft aliphatic polyurethane and the former is dipped into an aqueous dispersion of the first elastomer.

6. A method according to claim 1, wherein the coated former is dipped into a dispersion or a solution of the high modulus polyurethane in an aqueous or organic dispersant or solvent.

7. A surgeon's glove comprising an outer grip coating of a first elastomer on a high modulus polyurethane substrate, wherein the coating has a rough surface to provide a surface grip and the polyurethane substrate provides the majority of the glove's thickness.

8. A surgeon's glove according to claim 7, wherein the first elastomer is softer than the high modulus polyurethane substrate.

9. A surgeon's glove according to claim 7, wherein the first elastomer has a higher coefficient of friction than the high modulus polyurethane substrate.

10. The method according to claim 1 wherein said first elastomer comprises an organic solvent solution or dispersion having a viscosity of less than 800 cps (8 $Nm^{-2}s$) when measured in a Brookfield viscometer at a speed of 12 rpm using an LV2 spindle at 25° C.±2° C.

11. The method according to claim 1 wherein said first elastomer comprises an organic solvent solution or dispersion having a viscosity of less than 600 cps (6 $Nm^{-2}s$) when measured in a Brookfield viscometer at a speed of 12 rpm using an LV2 spindle at 25° C.±2° C.

12. The method according to claim 1 wherein said first elastomer is coated on said roughened former by dipping said roughened former into a dispersion or solution comprising said first elastomer.

13. A surgeon's glove comprising a grip coating of a first elastomer on a high modulus polyurethane substrate, said grip coating having a rough surface to provide surface grip, said first elastomer being softer than the high modulus polyurethane substrate and having a modulus of less than 3 MPa at 100% extension.

14. The surgeon's glove according to claim 13, wherein said first elastomer has a modulus of less than 2 MPa at 100% extension.

15. The surgeon's glove according to claim 13, wherein said first elastomer is predominantly hydrophobic.

16. The surgeon's glove according to claim 13, wherein said first elastomer comprises:

a soft polyurethane;

a block copolymer selected from the group consisting of styrene-isoprene-styrene and styrene-ethylene-butylene-styrene;

natural rubber;

polyvinylchloride;

a synthetic rubber selected from the group consisting of silicone rubber, acrylic rubber, nitrile rubber, polychloroprene rubber, and self-cross linking acrylonitrile latex; or a thermoset polymer.

17. The surgeon's glove according to claim 13, wherein said high modulus polyurethane substrate is a thermoplastic polyurethane.

18. The surgeon's glove according to claim 13, wherein said high modulus polyurethane substrate is at least 2 MPa at 100% extension.

19. The surgeon's glove according to claim 13, wherein the modulus of said high modulus polyurethane substrate is no greater than 5 MPa at 100% extension.

20. The surgeon's glove according to claim 13, wherein said high modulus polyurethane substrate is polyether polyurethane, polyester polyurethane, or polycaprolactone polyurethane.

* * * * *